US012778484B2

(12) United States Patent
Beeckler

(10) Patent No.: US 12,778,484 B2
(45) Date of Patent: Nov. 3, 2026

(54) INTUITIVE MAPPING SYSTEM

(71) Applicant: Biosense Webster (Israel) Ltd., Yokneam (IL)

(72) Inventor: Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 661 days.

(21) Appl. No.: 17/566,254

(22) Filed: Dec. 30, 2021

(65) Prior Publication Data

US 2023/0210437 A1 Jul. 6, 2023

(51) Int. Cl.

| | |
|---|---|
| ***A61B 5/367*** | (2021.01) |
| ***A61B 5/06*** | (2006.01) |
| ***A61B 5/287*** | (2021.01) |
| ***A61B 5/343*** | (2021.01) |

(52) U.S. Cl.

CPC .............. *A61B 5/367* (2021.01); *A61B 5/068* (2013.01); *A61B 5/287* (2021.01); *A61B 5/343* (2021.01)

(58) Field of Classification Search

CPC ......... A61B 5/367; A61B 5/343; A61B 5/287; A61B 5/068

See application file for complete search history.

(56) References Cited

U.S. PATENT DOCUMENTS

| | | | |
|---|---|---|---|
| 5,078,714 | A | 1/1992 | Katims |
| 5,341,807 | A | 8/1994 | Nardella |
| 5,391,199 | A | 2/1995 | Ben-Haim |
| 5,447,529 | A | 9/1995 | Marchlinski et al. |
| 5,469,857 | A | 11/1995 | Laurent et al. |
| 5,662,108 | A | 9/1997 | Budd et al. |
| 5,673,704 | A | 10/1997 | Marchlinski et al. |
| 5,836,874 | A | 11/1998 | Swanson et al. |
| 5,836,990 | A | 11/1998 | Li |
| 5,891,095 | A | 4/1999 | Eggers et al. |
| 5,935,079 | A | 8/1999 | Swanson et al. |
| 6,239,724 | B1 | 5/2001 | Doron et al. |
| 6,332,089 | B1 | 12/2001 | Acker et al. |

(Continued)

FOREIGN PATENT DOCUMENTS

| | | | |
|---|---|---|---|
| CA | 2285342 | C | 6/2007 |
| WO | 1996005768 | A1 | 2/1996 |

OTHER PUBLICATIONS

Extended European Search Report dated May 4, 2023, from corresponding European Application No. 22217063.1.

*Primary Examiner* — John R Downey

(57) ABSTRACT

In one exemplary mode, a medical system includes a catheter to be inserted into a chamber of a heart of a living subject, and including a distal end including catheter electrodes to contact tissue at respective locations within the chamber of the heart, at least one position sensor to provide at least one position signal indicative of at least one position of the distal end, a display, and processing circuitry to assess respective qualities of contact of the catheter electrodes with the tissue, compute positions of respective ones of the catheter electrodes responsively to the at least one position signal, generate a 3D anatomical map of at least part of the chamber of the heart responsively to the assessed respective qualities of contact and the computed positions of the respective ones of the catheter electrodes and render to the display the generated 3D anatomical map.

15 Claims, 4 Drawing Sheets

(56) References Cited

U.S. PATENT DOCUMENTS

| | | | | |
|---|---|---|---|---|
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 7,962,195 | B2 * | 6/2011 | Govari | A61B 8/0833 600/407 |
| 9,168,004 | B2 | 10/2015 | Gliner et al. | |
| 10,918,310 | B2 | 2/2021 | Cohen et al. | |
| 2002/0065455 | A1 | 5/2002 | Ben-Haim et al. | |
| 2003/0120150 | A1 | 6/2003 | Govari | |
| 2004/0068178 | A1 | 4/2004 | Govari | |
| 2007/0100332 | A1 | 5/2007 | Paul et al. | |
| 2009/0093806 | A1 | 4/2009 | Govari et al. | |
| 2009/0138007 | A1 | 5/2009 | Govari et al. | |
| 2010/0198041 | A1 * | 8/2010 | Christian | A61M 25/04 600/375 |
| 2013/0085416 | A1 | 4/2013 | Mest | |
| 2014/0180152 | A1 * | 6/2014 | Maskara | A61B 18/1492 600/509 |
| 2015/0133822 | A1 * | 5/2015 | Cathier | A61B 5/1076 600/595 |
| 2016/0331267 | A1 | 11/2016 | Maskara et al. | |
| 2018/0177552 | A1 * | 6/2018 | Zoabi | A61B 5/283 |
| 2020/0022653 | A1 | 1/2020 | Moisa | |
| 2020/0275977 | A1 * | 9/2020 | Govari | G06T 15/10 |
| 2020/0367829 | A1 * | 11/2020 | Govari | A61B 5/7221 |
| 2021/0077180 | A1 | 3/2021 | Govari et al. | |
| 2023/0008606 | A1 * | 1/2023 | Wekselman | A61B 8/461 |
| 2023/0157569 | A1 * | 5/2023 | Govari | A61B 5/367 600/374 |

* cited by examiner

INTUITIVE MAPPING SYSTEM

FIELD OF THE DISCLOSURE

The present disclosure relates to medical systems, and in particular, but not exclusively, to mapping a body part with a catheter device.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178 incorporated by reference herein. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser, pulsed field, and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied between the tip electrode(s) of the ablating catheter, and the reference electrode, flowing through the media between the electrodes it, i.e., blood and tissue. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, 2009/0093806 and 2009/0138007, whose disclosures are incorporated herein by reference describe methods of sensing contact pressure between the distal tip of a catheter and tissue in a body cavity using a force sensor embedded in the catheter.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342, all incorporated by reference herein. A number of these references, e.g., U.S. Pat. Nos. 5,935,079, 5,836,990, and 5,447,529 determine electrode-tissue contact by measuring the impedance between the tip electrode and a return electrode. As disclosed in the '529 patent, it is generally known than impedance through blood is generally lower that impedance through tissue. Accordingly, tissue contact has been detected by comparing the impedance values across a set of electrodes to premeasured impedance values when an electrode is known to be in contact with tissue and when it is known to be in contact only with blood.

U.S. Pat. No. 9,168,004 to Gliner, at al., which is herein incorporated by reference with a copy in the Appendix, describes using machine learning to determine catheter electrode contact. The '004 Patent describes cardiac catheterization being carried out by memorizing a designation of a contact state between an electrode of the probe and the heart wall as an in-contact state or an out-of-contact state, and making a series of determinations of an impedance phase angle of an electrical current passing through the electrode and another electrode, identifying maximum and minimum phase angles in the series, and defining a binary classifier adaptively as midway between the extremes. A test value is compared to the classifier as adjusted by a hysteresis factor, and a change in the contact state is reported when the test value exceeds or falls below the adjusted classifier.

US Patent Publication 2013/0085416 of Mest, which is herein incorporated by reference with a copy provided in the Appendix, describes a method for the in vivo re-calibration of a force sensing probe such as an electrophysiology catheter which provides for the generation of an auto zero zone. The distal tip of the catheter or other probe is placed in a body cavity within the patient. Verification that there is no tissue contact is made using electrocardiogram (ECG) or impedance data, fluoroscopy or other real-time imaging data and/or an anatomical mapping system. Once verification that there is no tissue contact made, the system recalibrates the signal emanating from the force sensor setting it to correspond to a force reading of zero grams and this recalibrated baseline reading is used to generate and display force readings based on force sensor data.

BRIEF DESCRIPTION OF THE DRAWINGS

The present disclosure will be understood from the following detailed description, taken in conjunction with the drawings in which.

DESCRIPTION OF EXEMPLARY MODES

Overview

Figure 1:
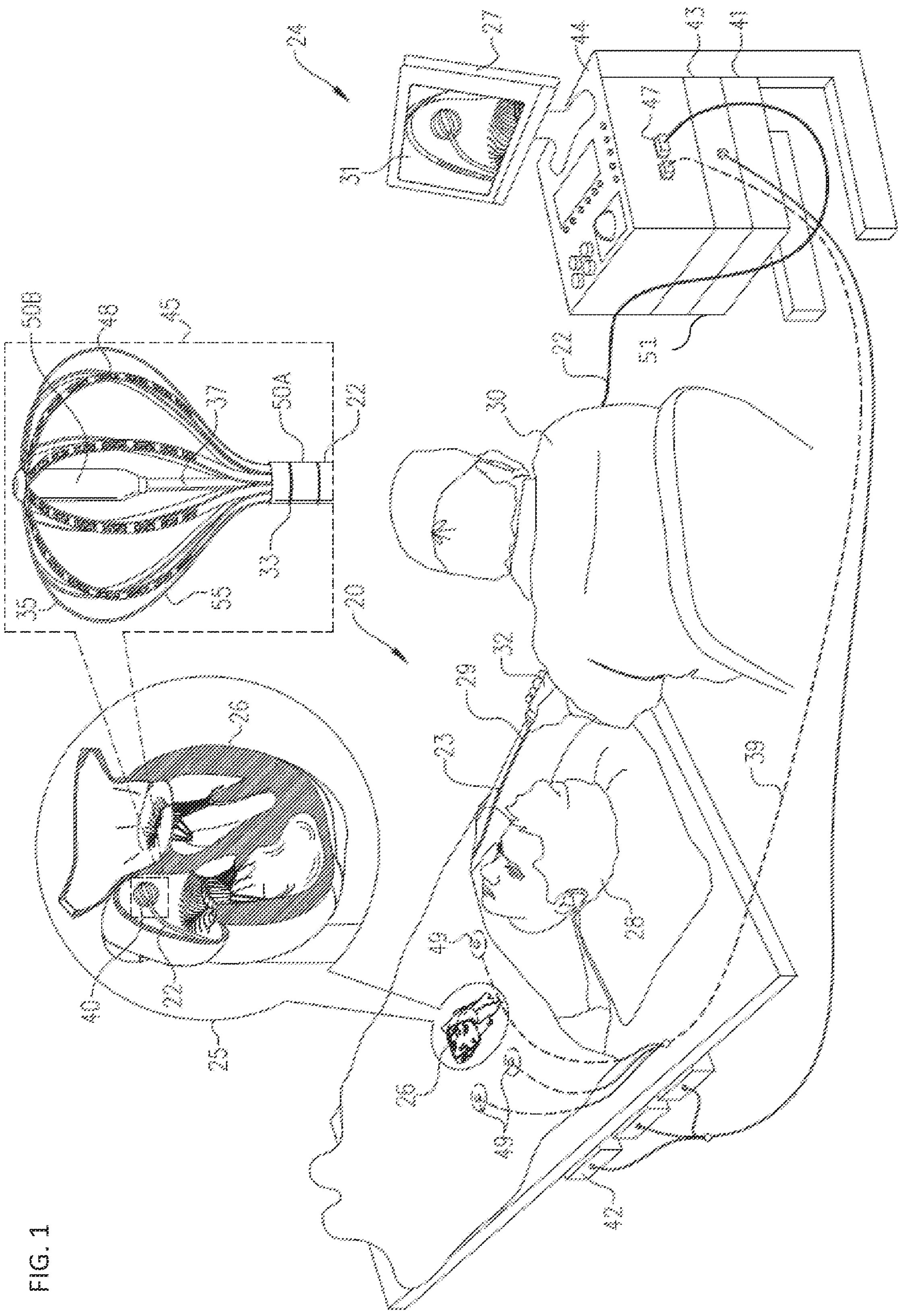
FIG. 1 is a schematic, pictorial illustration of a mapping system constructed and operative in accordance with an exemplary mode of the present disclosure.

During initially mapping a chamber of the heart, the physician positions a mapping catheter in the chamber. As the catheter is moved arbitrarily in the chamber, a processor acquires locations of electrodes on the catheter. The locations form a three-dimensional (3D) cloud of points, and the processor then joins the outermost points of the cloud, using a mapping algorithm such as fast anatomical mapping (FAM) to form a smooth shell. FAM is described in U.S. Pat. No. 10,918,310 to Cohen, et al., incorporated by reference with a copy provided in the Appendix.

As the points are acquired, the shell is built leading to an expanding shell as the catheter moves around the chamber. For example, if a basket catheter is used, the map will initially look like the form of the basket catheter until the basket is moved around leading to an expanded map. Therefore, as the map is being created some of the map surface is temporary and is removed in favor of a map surface generated by newly acquired points. This is confusing to the physician and therefore makes the mapping process more complicated, and lengthy, leading to accompanying problems.

Therefore, exemplary modes of the present disclosure provide a system that generates an anatomical map based on electrodes that are within sufficient contact with the tissue of the chamber of the heart. In this manner, the map walls that are generated are generally part of (or very similar to) the walls that are included in the final version of the anatomical map, so that the physician will not be confused by temporary map walls as the map is being built. The map will grow as the catheter is moved around the chamber, adding electrode positions of electrodes in sufficient contact with the tissue. Sufficient contact may be determined using a "quality of contact" discussed in more detail below.

This method is particularly, but not exclusively, suitable for use with catheters (e.g., basket and balloon catheters) where each electrode faces in one direction so that when sufficient electrode contact with tissue is detected, the position of the tissue in sufficient contact with the electrode is known with sufficient accuracy.

In some exemplary modes, the system finds a direction in which the physician could move the catheter to make the mapping process easier. The direction may be found based on the position of electrode(s) currently in sufficient contact with the tissue and the current position of the distal end of the catheter so that the direction points away from the tissue currently in sufficient contact with electrode(s) and points to another section of the chamber of the heart. An indicator (e.g., an arrow) is then rendered to a display over the anatomical map to suggest to the physician how to move the distal end of the catheter based on the found direction. In some exemplary modes, the direction may be found by drawing a line from (a center) of the electrode(s) in sufficient contact with the tissue to the center of the distal end assembly of the catheter (or to another point on the catheter). In some exemplary modes, the system checks if the direction points to an existing map portion. If the direction points to a map portion that already exists, the system adjusts the direction until the direction points to where an existing map portion does not exist.

Quality of contact is now discussed. In response to signals provided by the catheter, processing circuitry assesses the respective quality of contact of each of the catheter electrodes with the tissue in the heart. Any one of the catheter electrodes may be in full or partial contact with the tissue of the heart. In some cases, any one of the catheter electrodes may be in contact with the tissue via another fluid such as blood of various thicknesses. The quality of contact (full or partial contact, or contact via another liquid) of any one of the catheter electrodes with the tissue may be assessed based on the signals provided by the catheter.

The term "quality of contact" as used in the specification and claims is defined herein as a quantitative indicator of the degree of contact between one of the catheter electrodes and the tissue. The "quality of contact" may be expressed directly, for example in terms a measured electrical impedance, or indirectly, for example in terms of contact force, pressure or IEGM amplitude, as will now be described below in more detail.

In some exemplary modes, the catheter may provide signals which provide an indication of impedance between the catheter electrodes and body surface electrodes. The indication of the impedance provides an indication of a quality of contact, such that a higher value of impedance between one of the catheter electrodes and the body surface electrodes indicates a higher quality of contact between that catheter electrode and the tissue. A value of impedance may be selected to define a minimum quality of contact considered to represent sufficient contact between any one of the catheter electrodes and the tissue.

In some exemplary modes, the impedance between one of the catheter electrodes and another one of the electrodes on the catheter may be used as a measure of quality of contact. As disclosed in the '529 patent mentioned in the background section above, it is generally known that impedance through blood is generally lower than impedance through tissue. Accordingly, tissue contact may be assessed by comparing impedance values across a set of electrodes to premeasured impedance values when an electrode is known to be in sufficient contact with tissue and when it is known to be in contact only with blood.

In some exemplary modes, the method of U.S. Pat. No. 9,168,004 to Gliner, at al., which is herein incorporated by reference (with a copy provided in the Appendix) may be used to assess quality of contact using a machine learning based method.

In some exemplary modes, the catheter may provide signals from force or pressure sensors. The indication of force or pressure provides an indication of a quality of contact, such that a higher value of force or pressure indicates a higher quality of contact between a catheter electrode and the tissue. A value of force or pressure may be selected to define a minimum quality of contact considered to represent sufficient contact between any one of the catheter electrodes and the tissue.

In some exemplary modes, the sensed IEGM signals may be used to assess the quality of contact between any one of the catheter electrodes and the tissue. The maximum amplitude of the IEGM signal associated with one of the catheter electrodes is indicative of the quality of contact between that catheter electrode and the tissue, such that a higher value of the maximum amplitude of the IEGM signal indicates a higher quality of contact between that catheter electrode and the tissue. An amplitude value of the IEGM signal may be selected to define a minimum quality of contact considered to represent sufficient contact between any one of the catheter electrodes and the tissue.

System Description

Reference is now made to FIG. 1, which is a schematic, pictorial illustration of a mapping system 20, in accordance with an exemplary mode of the present disclosure. The system 20 includes a catheter 40 configured to be inserted into a body part (e.g., a chamber of a heart 26) of a living subject (e.g., a patient 28) seen in detail in inset 25. A physician 30 navigates the catheter 40 (for example, a basket catheter produced by Biosense Webster, Inc. of Irvine, CA, USA), seen in detail in inset 45, to a target location in the heart 26 of the patient 28, by manipulating a deflectable segment of an insertion tube 22 of the catheter 40, using a manipulator 32 near a proximal end 29 of the insertion tube 22, and/or deflection from a sheath 23. In the pictured exemplary mode, physician 30 uses catheter 40 to perform anatomical mapping of a cardiac chamber.

The catheter 40 includes a distal end 33. The distal end 33 of the catheter 40 includes an assembly 35 (e.g., a basket assembly as shown in FIG. 1 or a balloon assembly or any suitable distal end assembly) on which at least one (e.g., multiple) catheter electrode (s) 48 (only some labeled for the sake of simplicity) are disposed. The electrodes 48 are configured to contact tissue at respective locations within the chamber of the heart. The assembly 35 is disposed distally to the insertion tube 22 and may be connected to the insertion tube 22 via a coupling member of the insertion tube 22 at the distal end 33. The coupling member of the insertion tube 22 may be formed as an integral part of the rest of the insertion tube 22 or as a separate element which connects with the rest of the insertion tube 22.

The assembly 35 further comprises multiple flexible strips 55 (only two labeled for the sake of simplicity), to each of which are coupled the electrodes 48. The assembly 35 may include any suitable number of electrodes 48. In some exemplary modes, the assembly 35 may include ten flexible strips 55 and 120 electrodes, with twelve electrodes disposed on each flexible strip 55.

The catheter 40 includes a pusher 37. The pusher 37 is typically a tube that is disposed in a lumen of the insertion tube 22 and spans from the proximal end 29 to the distal end 33 of the insertion tube 22. A distal end of the pusher 37 is connected to distal ends of the flexible strips 55, typically via a coupling member of the pusher 37. The coupling member of the pusher 37 may be formed as an integral part of the rest of the pusher 37 or as a separate element which connects with the rest of the pusher 37. The distal end of the insertion tube 22 is connected to proximal ends of the flexible strips 55, typically via the coupling member of the distal end 33. The pusher 37 is generally controlled via the manipulator 32 to deploy the assembly 35 and change an ellipticity of the assembly 35 according to the longitudinal displacement of the pusher 37 with respect to the insertion tube 22. The actual basket assembly 35 structure may vary. For example, flexible strips 55 may be made of a printed circuit board (PCB), or of a shape-memory alloy, or any suitable material.

Exemplary modes described herein refer mainly to a basket distal-end assembly 35, purely by way of example. In alternative exemplary modes, the disclosed techniques can be used with a catheter having a balloon-based distal-end assembly or of any other suitable type of distal-end assembly.

Catheter 40 is inserted in a collapsed configuration, through sheath 23, and only after the catheter 40 exits sheath 23 is catheter 40 able to change shape by retracting pusher 37. By containing catheter 40 in a collapsed configuration, sheath 23 also serves to minimize vascular trauma on its way to the target location.

The distal end 33 of the catheter 40 comprises magnetic coil sensors 50A and 50B. The magnetic coil sensor 50A is shown in inset 45 at the distal edge of insertion tube 22 (i.e., at the proximal edge of basket assembly 35). The sensor 50A may be a Single-Axis Sensor (SAS), or a Double-Axis Sensor (DAS) or a Triple-Axis Sensor (TAS). Similarly, the sensor 50B may be a SAS, DAS, or TAS. Magnetic coil sensors 50A and 50B and electrodes 48 are connected by wires running through insertion tube 22 to various driver circuitries in a console 24.

In some exemplary modes, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance and angles between sensors 50A and 50B. Patient 28 is placed in a magnetic field generated by a pad containing multiple magnetic field generator coils 42, which are driven by a unit 43. The magnetic field generator coils 42 are configured to generate respective alternating magnetic fields, having respective different frequencies, into a region where a body-part (e.g., the heart 26) of a living subject (e.g., the patient 28) is located. The magnetic coil sensors 50A and 50B are configured to output electrical signals responsively to detecting the respective magnetic fields. For example, if there are nine magnetic field generator coils 42 generating nine respective different alternating magnetic fields with nine respective different frequencies, the electrical signals output by the magnetic coil sensors 50 will include components of the nine different frequency alternating magnetic fields. The magnitude of each of the magnetic fields varies with distance from the respective magnetic field generator coils 42 such that the location of the magnetic coil sensors 50 may be determined from the magnetic fields sensed by the magnetic coil sensors 50. Therefore, the transmitted alternating magnetic fields generate the electrical signals in sensors 50A and 50B, so that the electrical signals are indicative of position and orientation of the magnetic coil sensors 50.

The generated signals are transmitted to console 24 and become corresponding electrical inputs to processing circuitry 41. The processing circuitry 41 may use the signals to compute: the elongation and angle of the basket assembly 35, in order to estimate basket ellipticity, angle, and elongation/retraction state from the calculated distance and angles between sensors 50A and 50B; and compute a relative orientation between the axes of the sensors 50A and 50B to estimate a shape of the expandable distal end assembly 35 (e.g., a basket shape) responsively to the relative orientation, as described in more detail below.

The bow of the flexible strips 55 and/or the positions of the electrodes 48 (or other features) on the flexible strips 55 with respect to a fixed point on the catheter 40 (such as the distal tip of the insertion tube 22) may be measured for various distances between the magnetic sensors 50A, 50B and for various relative orientation angles between the magnetic sensors 50A, 50B. For example, the positions of the electrodes 48 with respect to the fixed point on the catheter 40 may be measured for every 0.2 mm movement of the pusher 37 with respect to the insertion tube 22 and for every 1 degree of relative orientation between the magnetic sensors 50A, 50B (up to a maximum sideways movement of the assembly 35). At each different distance/relative-orientation combination, the computed distance and computed relative orientation angle between the magnetic sensors 50A, 50B is recorded along with the position data of the electrodes 48. This data may then be used to estimate the bow of the flexible strips 55 and/or the positions of the electrodes 48 (or other features) on the flexible strips 55 with respect to a fixed point on the catheter 40 (such as the distal tip of the insertion tube 22) responsively to the computed distance and relative orientation angle between the magnetic sensors 50A, 50B.

Additionally, or alternatively, the bow of the flexible strips 55 may be estimated based on the following assumptions: (a) each of the flexible strips 55 is of a fixed and known length; (b) each of the flexible strips 55 is connected to the pusher 37 via a coupler, with the distal ends of the flexible strips 55 being substantially perpendicular (within an error of plus or minus 10 degrees) to the longitudinal axis of the insertion tube 22; (c) each of the flexible strips 55 is connected to the insertion tube 22 via a coupler, which couples the proximal ends of the flexible strips 55 to the insertion tube 22, substantially parallel (within an error of plus or minus 10 degrees) to the longitudinal axis of the insertion tube 22. Based on the above assumptions (a)-(c), and the computed positions of the couplers based on the computed positions of the magnetic sensors 50A, 50B, the bow of each of the flexible strips 55 may be computed using a third-degree polynomial. In some exemplary modes, the bow of the flexible strips 55 and/or the positions of the electrodes 48 (or other features) on the flexible strips 55 with respect to a fixed point on the catheter 40 (such as the distal tip of the insertion tube 22) may be computed based on the computed distance and orientation between the magnetic sensors 50A, 50B and a model of the catheter 40 which provides the bow of the flexible strips 55 and/or the positions of the electrodes 48 for the computed distance based on the mechanical properties and dimensions of the flexible strips 55.

A method of position and/or direction sensing using external magnetic fields and magnetic coil sensors, such as sensors 50A and 50B, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, all incorporated by reference herein.

In some exemplary modes, the processing circuitry 41 uses position-signals received from the electrodes 48 or body surface electrodes 49, and the magnetic sensor 50 to estimate a position of the assembly 35 inside a body part, such as inside a cardiac chamber. In some exemplary modes, the processing circuitry 41 correlates the position signals received from the electrodes 48, 49 with previously acquired magnetic location-calibrated position signals, to estimate the position of the assembly 35 inside the body part. The position coordinates of the electrodes 48 may be determined by the processing circuitry 41 based on, among other inputs, measured impedances, voltages or on proportions of currents distribution, between the electrodes 48 and the body surface electrodes 49.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1, all incorporated by reference herein.

The Carto®3 system applies Active Current Location (ACL) which is a hybrid current-distribution and magnetic-based position-tracking technology. In some exemplary modes, using ACL, the processing circuitry 41 estimates the positions of the electrodes 48. In some exemplary modes, the signals received from the electrodes 48, 49 are correlated with a current-to-position matrix (CPM) which maps current distribution ratios (or another electrical value) with a position that was previously acquired from magnetic location-calibrated position signals. The current distribution ratios are based on measurements of the body surface electrodes 49 of current flowing from the electrodes 48 to the body surface electrodes 49.

In some exemplary modes, to visualize catheters which do not include a magnetic sensor, the processing circuitry 41 may apply an electrical signal-based method, referred to as Independent Current Location (ICL) technology. In ICL, the processing circuitry 41 calculates a local scaling factor for each voxel of the volume in which catheters are visualized. The factor is determined using a catheter with multiple electrodes having a known spatial relationship, such as a lasso-shaped catheter. However, although yielding accurate local scaling (e.g., over several millimeters), ICL is less accurate when applied to a volume of a whole heart chamber, whose size is in the order of centimeters. The ICL method, in which positions are calculated based on current distribution proportions can have errors and may yield a distorted shape of the assembly 35, due to the non-linear nature of the current-based ICL space. In some exemplary modes, the processing circuitry 41 may apply the disclosed ICL method to scale ICL space and the assembly 35 shape into a correct one, based on known smaller scale distances between electrodes of a lasso-shaped catheter, for example, as well as based on larger scale distances, themselves based on the known distance between the electrodes 48 at the ends of the assembly 35.

Processing circuitry 41, typically part of a general-purpose computer, is further connected via a suitable front end and interface circuits 44, to receive signals from body surface-electrodes 49. Processing circuitry 41 is connected to surface-electrodes 49 by wires running through a cable 39 to the chest of patient 28. The catheter 40 includes a connector 47 disposed at the proximal end 29 of the insertion tube 22 for coupling to the processing circuitry 41.

In some exemplary modes, processing circuitry 41 renders to a display 27, a representation 31 of at least a part of the catheter 40 and an anatomical map or body-part, (e.g., from a mapping process or from a scan (e.g., CT or MRI) of the body-part previously registered with the system 20), responsively to computed position coordinates of the insertion tube 22 and the flexible strips 55.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. The system 20 may also include a memory 51 used by the processing circuitry 41.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2:
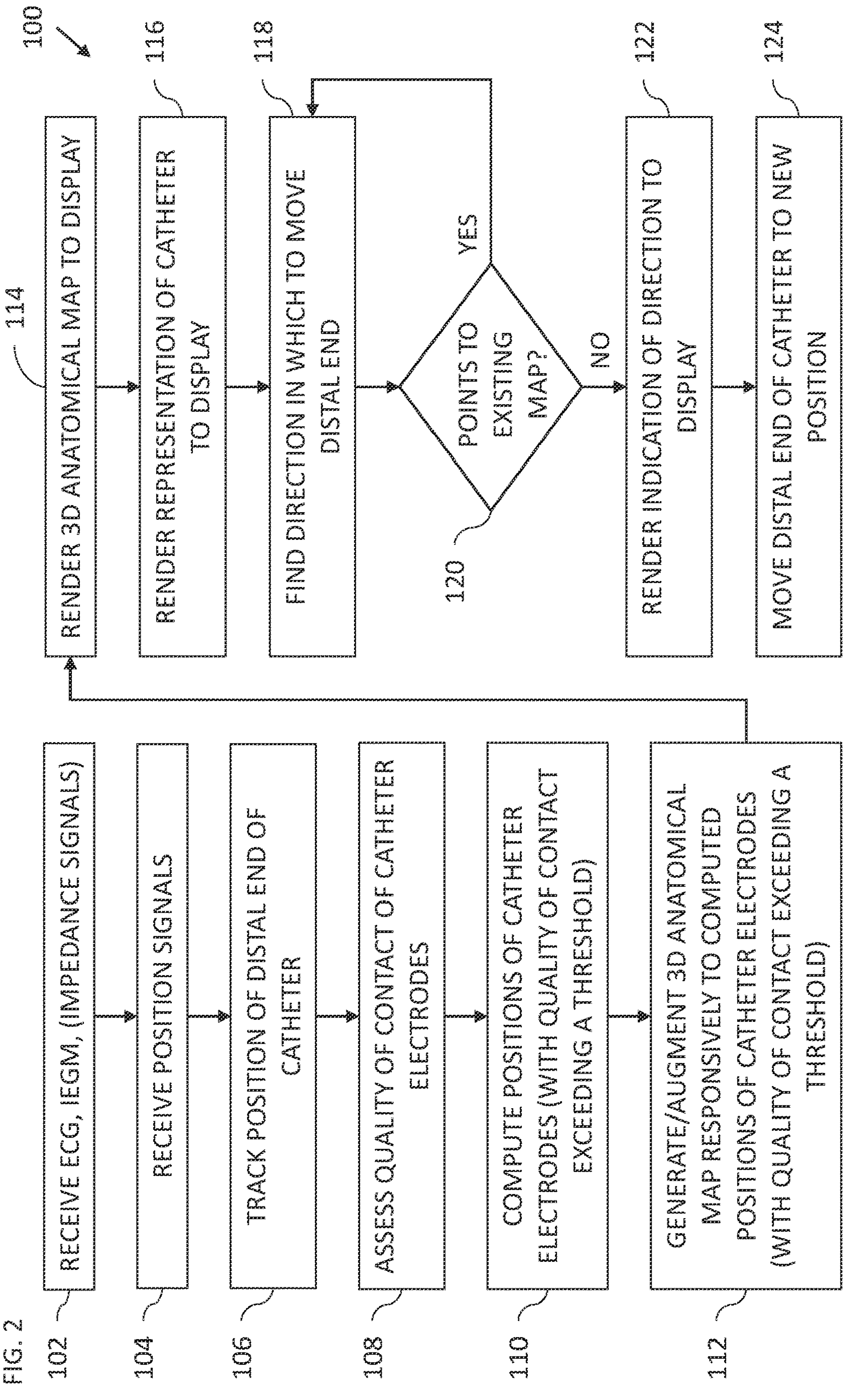
FIG. 2 is a flowchart including steps in a method of operation of the system of FIG. 1.
Figure 3:
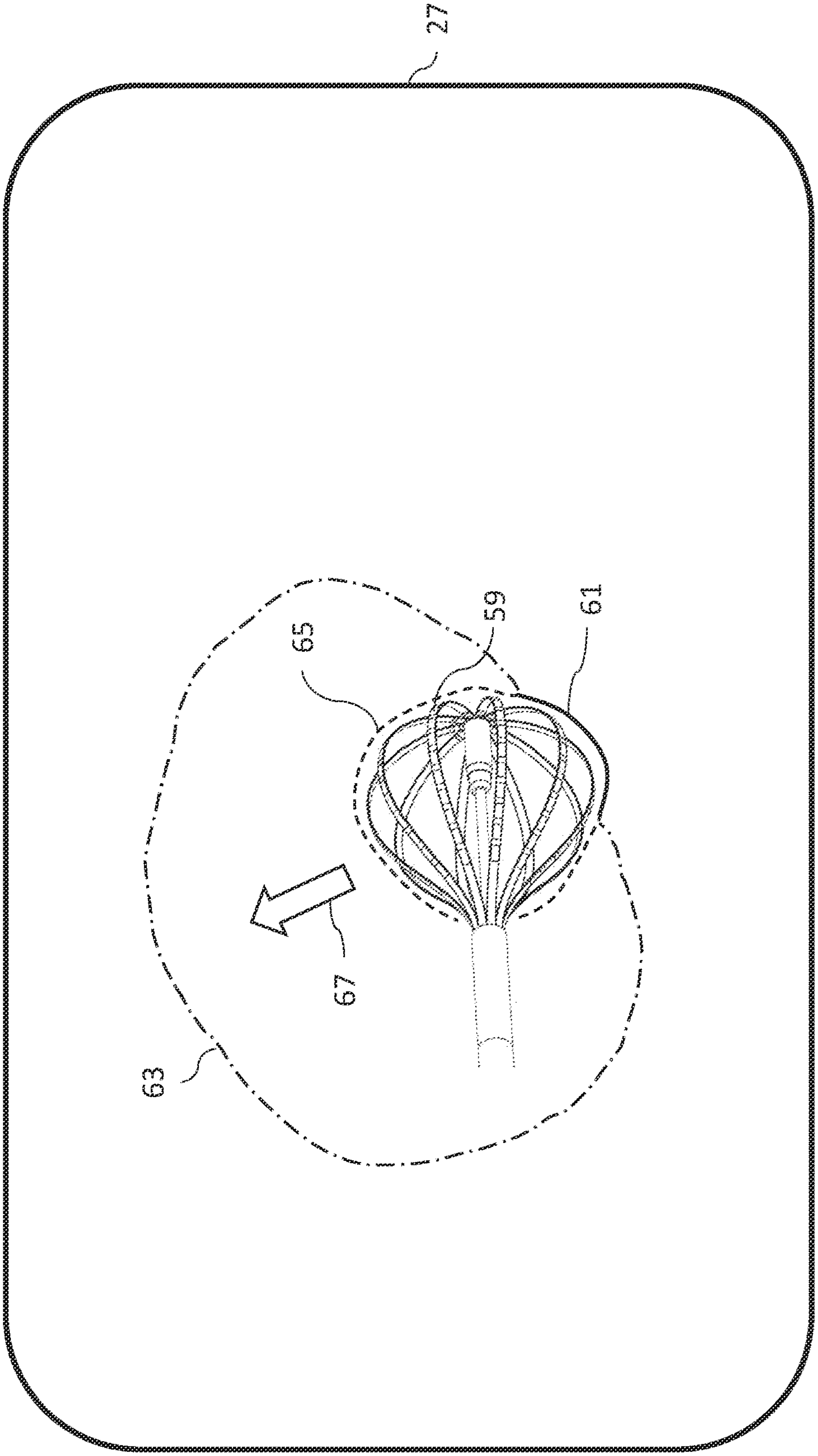
FIG. 3 is a schematic view of an initial anatomical map generated by the system of FIG. 1.

Reference is now made to FIG. 2, which is a flowchart 100 including steps in a method of operation of the system 20 of FIG. 1. Reference is also made to FIG. 3, which is a schematic view of an initial anatomical map 61 generated by the system 20 of FIG. 1.

The processing circuitry 41 is configured to receive signals provided by the catheter electrodes 48 and the body surface-electrodes 49. The provided signals may be indicative of electrocardiograms (ECGs), intracardiac electrograms (IEGMs), and impedance values between the catheter electrodes 48 and the body surface-electrodes 49 (block 102). The IEGMs and/or the impendence values may be used to assess the quality of contact described below.

As previously described with reference to FIG. 1, the position of the distal end of the catheter 40 may be found using a variety of methods, for example, based on signals provided by at least one position sensor, which may include the magnetic coil sensors 50 and/or the electrodes 48 and/or the body surface electrodes 49. The position sensor(s) 50, 48, 49 are configured to provide at least one position signal indicative of a position of the distal end 33. In some exemplary modes, the position of the distal end 33 of the catheter 40 may be found using imaging techniques such as ultrasonic scanning and suitable processing of the ultrasound images. The processing circuitry 41 is configured to receive the position signal(s) provided by the position sensor(s) 50, 48, 49 (block 104). The processing circuitry 41 is configured to track a position of the distal end 33 of the catheter 40 (e.g., compute a position of the distal end 33 of the catheter 40) responsively to the position signal (s) provided by the position sensor(s) 50, 48, 49 (block 106).

The processing circuitry 41 is configured to assess respective qualities of contact of the catheter electrodes 48 with the tissue of the chamber of the heart 26 (block 108). In other words, the processing circuitry 41 is configured to assess a quality of contact with each electrode 48 and the tissue.

Any one of the catheter electrodes 48 may be in full or partial contact with the tissue of the heart 26. In some cases, any one of the catheter electrodes 48 may be in contact with the tissue via another fluid such as blood of various thicknesses. The quality of contact (full or partial contact, or contact via another liquid) of any one of the catheter electrodes 48 with the tissue may be assessed based on the signals provided by the catheter 40.

As previously mentioned, the term "quality of contact" is a quantitative indicator of the degree of (electrical) contact between one of the catheter electrodes 48 and the tissue. The "quality of contact" may be expressed directly, for example in terms a measured electrical impedance, or indirectly, for example in terms of contact force, pressure or IEGM amplitude, as will now be described below in more detail.

In some exemplary modes, the catheter 40 may provide signals which provide an indication of impedance between the catheter electrodes 48 and the body surface electrodes 49. The indication of the impedance provides an indication of a quality of contact, such that a higher value of impedance between one of the catheter electrodes 48 and the body surface electrodes 49 indicates a higher quality of contact between that catheter electrode 48 and the tissue. A value of impedance may be selected to define a minimum quality of contact considered to represent sufficient contact between any one of the catheter electrodes 48 and the tissue.

In some exemplary modes, the impedance between one of the catheter electrodes 48 and another one of the electrodes on the catheter 40 may be used as a measure of quality of contact. As disclosed in the '529 patent mentioned in the background section above, it is generally known that impedance through blood is generally lower than impedance through tissue. Accordingly, tissue contact may be assessed by comparing impedance values across a set of electrodes to premeasured impedance values when an electrode is known to be in sufficient contact with tissue and when it is known to be in contact only with blood.

In some exemplary modes, the method of U.S. Pat. No. 9,168,004 to Gliner, at al., which is herein incorporated by reference, may be used to assess quality of contact. The '004 Patent describes using machine learning to determine catheter electrode contact. The '004 Patent describes cardiac catheterization being carried out by memorizing a designation of a contact state between an electrode of the probe and the heart wall as an in-contact state or an out-of-contact state, and making a series of determinations of an impedance phase angle of an electrical current passing through the electrode and another electrode, identifying maximum and minimum phase angles in the series, and defining a binary classifier adaptively as midway between the extremes. A test value is compared to the classifier as adjusted by a hysteresis factor, and a change in the contact state is reported when the test value exceeds or falls below the adjusted classifier.

In some exemplary modes, the catheter 40 may provide signals from force or pressure sensors (not shown), disposed at different locations on the flexible strips 55, that provide an indication of force or pressure exerted by the catheter electrodes 48 on the tissue. The indication of force or pressure provides an indication of a quality of contact, such that a higher value of force or pressure indicates a higher quality of contact between that catheter electrode 48 and the tissue. A value of force or pressure may be selected to define a minimum quality of contact considered to represent sufficient contact between any one of the catheter electrodes 48 and the tissue. These exemplary modes, may use any suitable force or pressure sensors as well as any suitable method for measuring the force or pressure, including any of the Patents or Patent Publications mentioned in the background section including the method described in US Patent Publication 2013/0085416 of Mest, which is herein incorporated by reference, and describes a method for the in vivo recalibration of a force sensing probe such as an electrophysiology catheter which provides for the generation of an auto zero zone. The distal tip of the catheter or other probe is placed in a body cavity within the patient. Verification that there is no tissue contact is made using electrocardiogram (ECG) or impedance data, fluoroscopy or other real-time imaging data and/or an anatomical mapping system. Once verification that there is no tissue contact made, the system recalibrates the signal emanating from the force sensor setting it to correspond to a force reading of zero grams and this recalibrated baseline reading is used to generate and display force readings based on force sensor data.

In some exemplary modes, intracardiac electrogram (IEGM) signals generated by the processing circuitry 41 may be used to assess the quality of contact between any one of the catheter electrodes 48 and the tissue. The maximum amplitude of the IEGM signal associated with one of the catheter electrodes 48 is indicative of the quality of contact between that catheter electrode 48 and the tissue, such that a higher value of the maximum amplitude of the IEGM signal indicates a higher quality of contact between that catheter electrode 48 and the tissue. An amplitude value of the IEGM signal may be selected to define a minimum quality of contact considered to represent sufficient contact between any one of the catheter electrodes 48 and the tissue.

The processing circuitry 41 is configured to compute positions of respective ones of the catheter electrodes 48 responsively to the position signal(s) from one or more of the position sensors 50, 48, 49 (block 110). The positions of the catheter electrode 48 may be computed using any suitable method, for example, the ACL or ICL methods described above. In some exemplary modes, the positions of the catheter electrode 48 may be computed based on a computed position of one or more of the magnetic coil sensors 50 based on a fixed geometrical relationship between the magnetic coil sensor(s) 50 and the catheter electrode 48.

In some exemplary modes, the processing circuitry 41 is configured to compute the positions of respective ones of the catheter electrodes 48 responsively to the respective catheter electrodes 48 having the assessed respective qualities of contact exceeding a threshold quality of contact. In other words, in some exemplary modes, the processing circuitry 41 only computes the positions of the catheter electrode 48 in sufficient contact with the tissue (i.e., with an assessed quality of contact above the threshold quality of contact).

The processing circuitry 41 is configured to generate a three-dimensional (3D) anatomical map 61 (FIG. 3) of at least part of the chamber of the heart 26 responsively to the assessed respective qualities of contact and the computed positions of the respective ones of the catheter electrodes 48 (block 112). In some exemplary modes, the processing circuitry 41 is configured to generate the 3D anatomical map 61 responsively to the computed positions of respective ones of the catheter electrodes 48 having the assessed respective qualities of contact exceeding the threshold quality of contact.

In some exemplary modes, the processing circuitry 41 is configured to generate the 3D anatomical map 61 responsively to the computed positions of the respective ones of the catheter electrodes 48 only having the assessed respective qualities of contact exceeding a threshold quality of contact. In other words, in some exemplary modes, the processing circuitry 41 only generates the anatomical map 61 from the positions of the catheter electrode 48 in sufficient contact with the tissue (i.e., with an assessed quality of contact above the threshold quality of contact) while the positions of electrodes 48 below the threshold quality of contact are excluded from being used to generate the map 61. The processing circuitry 41 may use any suitable algorithm to build a shell from the positions of the electrodes in sufficient contact with the tissue, for example, the FAM algorithm mentioned above.

The processing circuitry 41 is configured to render to the display 27 the generated 3D anatomical map 61 (block 114). The processing circuitry 41 is configured to render to the display 27 a representation 59 of the catheter 40 responsively to the tracked position of the distal end 33 of the catheter 40 (block 116).

The anatomical map 61 shown in FIG. 3 is a partial map representing a map built from electrodes 48 in sufficient contact with the tissue of the chamber of the heart 26. A dashed-dotted line 63 represents an approximate extent of the chamber of the heart. A dashed line 65 and the anatomical map 61 together represent the map that would be currently generated if the positions of all the catheter electrode 48 (even those not in sufficient contact with the tissue) were used in generating an anatomical map.

In some exemplary modes, the processing circuitry 41 is configured to find a direction in which to move the distal end 33 of the catheter 40 to make the mapping process easier for the physician 30. The direction may be found based on the position of electrode(s) 48 currently in sufficient contact with the tissue and the current position of the distal end 33 of the catheter 40 so that the direction points away from the tissue currently in sufficient contact with electrode(s) 48 and points to another section of the chamber of the heart 26. In some exemplary modes, the direction may be found by drawing a line from (a center) of the electrode(s) 48 in sufficient contact with the tissue to the center of the distal end assembly 35 of the catheter 40 (or to another point of the catheter 40).

Therefore, in some exemplary modes, the processing circuitry 41 is configured to find the direction in which to move the distal end 33 of the catheter 40 (away from the tissue currently in sufficient contact with the distal end of the catheter 40) responsively to: the tracked position of the distal end 33 of the catheter 40 (as the tracked position provides a region which is definitely in the chamber of the heart 26); and at least one of the catheter electrodes 48 having the assessed respective qualities of contact exceeding the threshold quality of contact (providing the catheter electrode 48 currently in sufficient contact (or most recently in contact) with the tissue) (block 118).

In some exemplary modes, at a decision block 120 the processing circuitry 41 is configured to check if the found direction points to an existing map portion of the anatomical map 61. If the direction points to an existing map portion, the processing circuitry 41 is configured to adjust the direction (e.g., randomly or by moving the direction in increasing circles around the original direction) at the step of block 118 until the direction points to a direction in which an existing map portion does not exist. The processing circuitry 41 is configured to render to the display 27 (with the representation 59 of the catheter 40 and the anatomical map 61) an indication 67 (e.g., an arrow) of the direction in which to move the distal end 33 of the catheter 40 responsively to the found direction (block 122).

Figure 4:
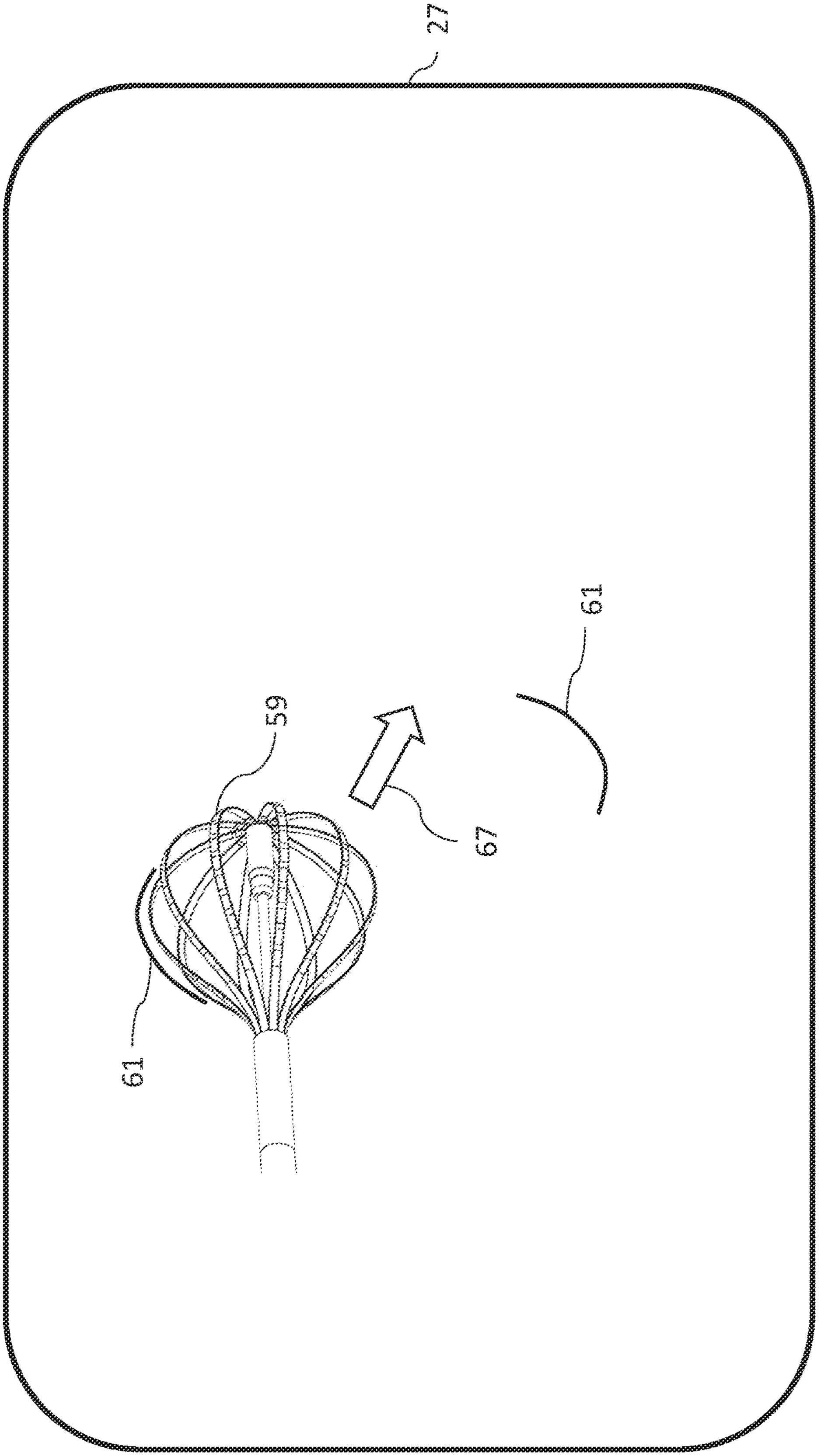
FIG. 4 is a schematic view of an augmented anatomical map generated by the system of FIG. 1.

Reference is now made to FIG. 4, which is a schematic view of the augmented anatomical map 61 generated by the system 20 of FIG. 1. Reference is also made to FIG. 2. The physician 30 moves the distal end 33 of the catheter 40 in the direction indicated by the indication 67 or any direction that the physician 30 decides (block 124). In the new position of the distal end 33 of the catheter 40, the steps of blocks 102-122 are repeated. Among the steps performed in the new position of the distal end 33 of the catheter 40 in the chamber of the heart 26, the processing circuitry 41 is configured to: assess respective new qualities of contact of respective ones of the catheter electrodes 48 with the tissue; compute new positions of respective ones of the catheter electrodes 48 responsively to the position signal(s); augment the 3D anatomical map 61 responsively to the assessed respective new qualities of contact and the computed new positions of the respective ones of the catheter electrodes 48; and render to the display 27 the augmented 3D anatomical map 61. FIG. 4 also shows the indication 67 pointing in a different direction into the chamber of the heart 26 and away from the tissue currently in contact with the catheter electrode 48.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Examples are now listed below.

Example 1: A medical system (20), comprising: a catheter (40) configured to be inserted into a chamber of a heart (26) of a living subject, and including a distal end (33) comprising catheter electrodes (48) configured to contact tissue at respective locations within the chamber of the heart; at least one position sensor (50) configured to provide at least one position signal indicative of at least one position of the distal end; a display (27); and processing circuitry (41) configured to: assess respective qualities of contact of the catheter electrodes with the tissue; compute positions of respective ones of the catheter electrodes responsively to the at least one position signal; generate a three-dimensional (3D) anatomical map (61) of at least part of the chamber of the heart responsively to the assessed respective qualities of contact and the computed positions of the respective ones of the catheter electrodes and render to the display the generated 3D anatomical map.

Example 2: The system according to example 1, wherein the processing circuitry is configured to compute the positions of the respective ones of the catheter electrodes responsively to the respective ones of the catheter electrodes having the assessed respective qualities of contact exceeding a threshold quality of contact.

Example 3: The system according to example 1 or 2, wherein the processing circuitry is configured to generate the 3D anatomical map responsively to the computed positions of the respective ones of the catheter electrodes having the assessed respective qualities of contact exceeding a threshold quality of contact.

Example 4: The system according to any of examples 1-3, wherein the processing circuitry is configured to generate the 3D anatomical map responsively to the computed positions of the respective ones of the catheter electrodes only having the assessed respective qualities of contact exceeding a threshold quality of contact.

Example 5: The system according to any of examples 1-4, wherein the processing circuitry is configured to track a position of the distal end of the catheter responsively to the at least one position signal.

Example 6: The system according to example 5, wherein the processing circuitry is configured to render to the display a representation (59) of the catheter responsively to the tracked position of the distal end.

Example 7: The system according to example 5 or 6, wherein the processing circuitry is configured to: find a direction in which to move the distal end of the catheter responsively to: the tracked position of the distal end; and at least one of the catheter electrodes having the assessed respective qualities of contact exceeding the threshold quality of contact; and render to the display an indication (67) of the direction in which to move the distal end of the catheter.

Example 8: The system according to example 7, wherein the processing circuitry is configured to find the direction in which to move the distal end of the catheter away from the tissue currently in contact with the distal end of the catheter.

Example 9: The system according to example 7 or 8, wherein the processing circuitry is configured to: assess respective new qualities of contact of respective ones of the catheter electrodes with the tissue with the distal end of the catheter at a new position in the chamber of the heart; compute new positions of respective ones of the catheter electrodes responsively to the at least one position signal and the distal end of the catheter being at the new position in the chamber in the heart; augment the 3D anatomical map responsively to the assessed respective new qualities of contact and the computed new positions of the respective ones of the catheter electrodes; and render to the display the augmented 3D anatomical map of the chamber of the heart.

Example 10: The system according to any of examples 1-9, wherein the processing circuitry is configured to: assess respective new qualities of contact of respective ones of the catheter electrodes with the tissue with the distal end of the catheter at a new position in the chamber of the heart; compute new positions of respective ones of the catheter electrodes responsively to the at least one position signal and the distal end of the catheter being at the new position in the chamber in the heart; augment the 3D anatomical map responsively to the assessed respective new qualities of contact and the computed new positions of the respective ones of the catheter electrodes; and render to the display the augmented 3D anatomical map of the chamber of the heart.

Example 11: A medical method, comprising: providing at least one position signal indicative of at least one position of a distal end of a catheter inserted into a chamber of a heart of a living subject; assessing respective qualities of contact of catheter electrodes with the tissue; computing positions of respective ones of the catheter electrodes responsively to the at least one position signal; generating a three-dimensional (3D) anatomical map of at least part of the chamber of the heart responsively to the assessed respective qualities of contact and the computed positions of the respective ones of the catheter electrodes and rendering to a display the generated 3D anatomical map.

Example 12: The method according to example 11, wherein the computing includes computing the positions of the respective ones of the catheter electrodes responsively to the respective ones of the catheter electrodes having the assessed respective qualities of contact exceeding a threshold quality of contact.

Example 13: The method according to example 11 or 12, wherein the generating includes generating the 3D anatomical map responsively to the computed positions of the respective ones of the catheter electrodes having the assessed respective qualities of contact exceeding a threshold quality of contact.

Example 14: The method according to any of examples 11-13, wherein the generating includes generating the 3D anatomical map responsively to the computed positions of the respective ones of the catheter electrodes only having the assessed respective qualities of contact exceeding a threshold quality of contact.

Example 15: The method according to example 11, further comprising tracking a position of the distal end of the catheter responsively to the at least one position signal.

Example 16: The method according to example 15, further comprising rendering to the display a representation of the catheter responsively to the tracked position of the distal end.

Example 17: The method according to example 15 or 16, further comprising: finding a direction in which to move the distal end of the catheter responsively to: the tracked position of the distal end; and at least one of the catheter electrodes having the assessed respective qualities of contact exceeding a threshold quality of contact; and rendering to the display an indication of the direction in which to move the distal end of the catheter.

Example 18: The method according to example 17, wherein the finding includes finding the direction in which to move the distal end of the catheter away from the tissue currently in contact with the distal end of the catheter.

Example 19: The method according to example 17 or 18, further comprising: assessing respective new qualities of contact of respective ones of the catheter electrodes with the tissue with the distal end of the catheter at a new position in the chamber of the heart; computing new positions of respective ones of the catheter electrodes responsively to the at least one position signal and the distal end of the catheter being at the new position in the chamber in the heart; augmenting the 3D anatomical map responsively to the assessed respective new qualities of contact and the computed new positions of the respective ones of the catheter electrodes; and rendering to the display the augmented 3D anatomical map of the chamber of the heart.

Example 20: The method according to any of examples 11-19, further comprising: assessing respective new qualities of contact of respective ones of the catheter electrodes with the tissue with the distal end of the catheter at a new position in the chamber of the heart; computing new positions of respective ones of the catheter electrodes responsively to the at least one position signal and the distal end of the catheter being at the new position in the chamber in the heart; augmenting the 3D anatomical map responsively to the assessed respective new qualities of contact and the computed new positions of the respective ones of the catheter electrodes; and rendering to the display the augmented 3D anatomical map of the chamber of the heart.

Example 21: A software product, comprising a non-transient computer-readable medium in which program instructions are stored, which instructions, when read by a central processing unit (CPU), cause the CPU to: compute positions of respective ones of catheter electrodes of a catheter responsively to at least one position signal providing at least one position signal indicative of at least one position of a distal end of the catheter inserted into a chamber of a heart of a living subject; assess respective qualities of contact of the catheter electrodes with the tissue; generate a three-dimensional (3D) anatomical map of at least part of the chamber of the heart responsively to the assessed respective qualities of contact and the computed positions of the respective ones of the catheter electrodes; and render to a display the generated 3D anatomical map.

Various features of the disclosure which are, for clarity, described in the contexts of separate exemplary modes may also be provided in combination in a single exemplary mode. Conversely, various features of the disclosure which are, for brevity, described in the context of a single exemplary mode may also be provided separately or in any suitable sub-combination.

The exemplary modes described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

What is claimed is:

1. A medical system, comprising:

a catheter configured to be inserted into a chamber of a heart of a living subject, and including a distal end comprising catheter electrodes configured to contact tissue at respective locations within the chamber of the heart;

at least one position sensor configured to provide at least one position signal indicative of at least one position of the distal end;

a display; and processing circuitry configured to:

assess respective qualities of contact of the catheter electrodes with the tissue;

compute positions of respective ones of the catheter electrodes responsively to the at least one position signal;

generate a three-dimensional (3D) anatomical map of at least part of the chamber of the heart in response to the assessed respective qualities of contact and the computed positions of the respective ones of the catheter electrodes in which the qualities of contact exceed a threshold quality of contact;

render to the display the generated 3D anatomical map;

track a position of the distal end of the catheter responsively to the at least one position signal;

find a direction in which to move the distal end of the catheter responsively to (i) the tracked position of the distal end and (ii) at least one of the catheter electrodes having the assessed respective qualities of contact exceeding the threshold quality of contact by drawing a line from a center of the at least one of the catheter electrodes to a center of the distal end;

check if the found direction points to an existing map portion of the generated 3D anatomical map;

in response to the found direction pointing to the existing map portion, adjust the found direction by moving the found direction in increasing circles relative to the found direction until the adjusted found direction is to an unmapped portion of the generated 3D anatomical map; and render to the display an indication of the found direction or the adjusted found direction in which to move the distal end of the catheter, the found direction or the adjusted found direction being away from the tissue currently in contact with the distal end of the catheter.

2. The system according to claim 1, wherein the processing circuitry is configured to compute the positions of the respective ones of the catheter electrodes responsively to the respective ones of the catheter electrodes having the assessed respective qualities of contact exceeding the threshold quality of contact.

3. The system according to claim 1, wherein the processing circuitry is configured to generate the 3D anatomical map responsively to only the computed positions of the respective ones of the catheter electrodes having the assessed respective qualities of contact exceeding the threshold quality of contact, such that the computed positions of the respective ones of the catheter electrodes in which the qualities of contact are below the threshold quality of contact are excluded from being used to generate the 3D anatomical map.

4. The system according to claim 1, wherein the processing circuitry is configured to render to the display a representation of the catheter responsively to the tracked position of the distal end.

5. The system according to claim 1, wherein the processing circuitry is configured to:

assess respective new qualities of contact of respective ones of the catheter electrodes with the tissue with the distal end of the catheter at a new position in the chamber of the heart;

compute new positions of respective ones of the catheter electrodes responsively to the at least one position signal and the distal end of the catheter being at the new position in the chamber in the heart;

augment the 3D anatomical map responsively to the assessed respective new qualities of contact and the computed new positions of the respective ones of the catheter electrodes; and render to the display the augmented 3D anatomical map of the chamber of the heart.

6. The medical system according to claim 1, wherein the indication comprises an arrow.

7. A medical method, comprising:

providing at least one position signal indicative of at least one position of a distal end of a catheter inserted into a chamber of a heart of a living subject;

assessing respective qualities of contact of catheter electrodes with tissue;

computing positions of respective ones of the catheter electrodes responsively to the at least one position signal;

generating a three-dimensional (3D) anatomical map of at least part of the chamber of the heart responsively to the assessed respective qualities of contact and the computed positions of the respective ones of the catheter electrodes in which the qualities of contact exceed a threshold quality of contact;

rendering to a display the generated 3D anatomical map;

tracking a position of the distal end of the catheter responsively to the at least one position signal;

finding a direction in which to move the distal end of the catheter responsively to (i) the tracked position of the distal end and (ii) at least one of the catheter electrodes having the assessed respective qualities of contact exceeding a threshold quality of contact by drawing a line from a center of the at least one of the catheter electrodes to a center of the distal end;

checking if the found direction points to an existing map portion of the generated 3D anatomical map;

if the found direction points to the existing map portion, adjusting the found direction by moving the found direction in increasing circles relative to the found direction until the adjusted found direction is to an unmapped portion of the generated 3D anatomical map; and rendering to the display an indication of the found direction or the adjusted found direction in which to move the distal end of the catheter, the found direction or the adjusted found direction being away from the tissue currently in contact with the distal end of the catheter.

8. The method according to claim 7, wherein the computing includes computing the positions of the respective ones of the catheter electrodes responsively to the respective ones of the catheter electrodes having the assessed respective qualities of contact exceeding the threshold quality of contact.

9. The method according to claim 7, wherein the generating includes generating the 3D anatomical map responsively to only the computed positions of the respective ones of the catheter electrodes having the assessed respective qualities of contact exceeding the threshold quality of contact, such that the computed positions of the respective ones of the catheter electrodes in which the qualities of contact are below the threshold quality of contact are excluded from being used to generate the 3D anatomical map.

10. The method according to claim 7, further comprising rendering to the display a representation of the catheter responsively to the tracked position of the distal end.

11. The method according to claim 7, further comprising:

assessing respective new qualities of contact of respective ones of the catheter electrodes with the tissue with the distal end of the catheter at a new position in the chamber of the heart;

computing new positions of respective ones of the catheter electrodes responsively to the at least one position signal and the distal end of the catheter being at the new position in the chamber in the heart;

augmenting the 3D anatomical map responsively to the assessed respective new qualities of contact and the computed new positions of the respective ones of the catheter electrodes; and rendering to the display the augmented 3D anatomical map of the chamber of the heart.

12. The method according to claim 7, wherein the indication comprises an arrow.

13. A software product, comprising a non-transient computer-readable medium in which program instructions are stored, which instructions, when read by a central processing unit (CPU), cause the CPU to:

compute positions of respective ones of catheter electrodes of a catheter responsively to at least one position signal providing at least one position signal indicative of at least one position of a distal end of the catheter inserted into a chamber of a heart of a living subject;

assess respective qualities of contact of the catheter electrodes with tissue;

generate a three-dimensional (3D) anatomical map of at least part of the chamber of the heart responsively to the computed positions of the respective ones of the catheter electrodes having the assessed respective qualities of contact exceeding a threshold quality of contact;

render to a display the generated 3D anatomical map;

track a position of the distal end of the catheter responsively to the at least one position signal;

find a direction in which to move the distal end of the catheter responsively to (i) the tracked position of the distal end, and (ii) at least one of the catheter electrodes having the assessed respective qualities of contact exceeding the threshold quality of contact by drawing a line from a center of the at least one of the catheter electrodes to a center of the distal end;

check if the found direction points to an existing map portion of the generated 3D anatomical map;

in response to the found direction pointing to the existing map portion, adjust the found direction by moving the found direction in increasing circles relative to the found direction until the adjusted found direction is to an unmapped portion of the generated 3D anatomical map; and render to the display an indication of the found direction or the adjusted found direction in which to move the distal end of the catheter, the found direction or the adjusted found direction being away from the tissue currently in contact with the distal end of the catheter.

14. The software product according to claim 13, wherein the instructions, when read by the CPU, cause the CPU to:

generate the 3D anatomical map responsively to only the computed positions of the respective ones of the catheter electrodes having the assessed respective qualities of contact exceeding the threshold quality of contact, such that the computed positions of the respective ones of the catheter electrodes in which the qualities of contact are below the threshold quality of contact are excluded from being used to generate the 3D anatomical map.

15. The software product according to claim 13, wherein the indication comprises an arrow.

* * * * *